US010098879B2

(12) United States Patent
Malvy et al.

(10) Patent No.: US 10,098,879 B2
(45) Date of Patent: Oct. 16, 2018

(54) METHODS AND PHARMACEUTICAL COMPOSITIONS FOR THE TREATMENT OF EBOLA VIRUS DISEASE

(71) Applicants: INSERM (INSTITUT NATIONAL DE LA SANTÉ ET DE LA RECHERCHE MÉDICALE), Paris (FR); Xavier Anglaret, Bordeaux (FR); UNIVERSITÉ DE BORDEAUX, Bordeaux (FR); CHU DE BOURDEAUX, Talance (FR); TOYAMA CHEMICAL CO., LTD, Tokyo (JP)

(72) Inventors: Denis Malvy, Bordeaux (FR); Sylvain Baize, Lyons (FR); Xavier De Lamballerie, Marseille (FR); Hervé Raoul, Lyons (FR); Cédric Laouenan, Paris (FR); Jeremie Guedj, Paris (FR); France Mentre, Paris (FR)

(73) Assignees: INSERM (INSTITUT NATIONAL DE LA SANTÉ ET DE LA RECHERCHE MÉDICALE), Paris (FR); UNIVERSITÉ DE BORDEAUX, Bordeaux (FR); CHU DE BORDEAUX, Talance (FR); TOYAMA CHEMICAL CO., LTD, Tokyo (JP)

( * ) Notice: Subject to any disclaimer, the term of this patent is extended or adjusted under 35 U.S.C. 154(b) by 0 days.

(21) Appl. No.: 15/546,362

(22) PCT Filed: Jan. 27, 2016

(86) PCT No.: PCT/EP2016/051645
§ 371 (c)(1),
(2) Date: Jul. 26, 2017

(87) PCT Pub. No.: WO2016/120301
PCT Pub. Date: Aug. 4, 2016

(65) Prior Publication Data

US 2018/0021333 A1 Jan. 25, 2018

(30) Foreign Application Priority Data

Jan. 28, 2015 (WO) .................. PCT/IB2015/000334
Feb. 19, 2015 (WO) .................. PCT/IB2015/000351

(51) Int. Cl.
*A61K 31/4965* (2006.01)
*C12Q 1/70* (2006.01)

(52) U.S. Cl.
CPC .......... *A61K 31/4965* (2013.01); *C12Q 1/701* (2013.01)

(58) Field of Classification Search
None
See application file for complete search history.

(56) References Cited

PUBLICATIONS

Oestereich et al., Antiviral Research (2014), 105, pp. 17-21.*
Smither et al., Antiviral Research (2014), 104, pp. 153-155.*

* cited by examiner

*Primary Examiner* — Brian J Davis
(74) *Attorney, Agent, or Firm* — Witham & Cook, P.C.

(57) ABSTRACT

The invention relates to methods and pharmaceutical compositions for the treatment of Ebola Virus Disease. In particular the present relates to a method of treating Ebola Virus Disease in a subject in need thereof comprising administering the subject with a therapeutically effective amount of Favipiravir.

3 Claims, 6 Drawing Sheets

|  | JIKI trial database † | | | | Gueckedou database* | | | | P** |
|---|---|---|---|---|---|---|---|---|---|
|  | Cured | | Dead | | Cured | | Dead | | |
|  | N | (%) | N | (%) | N | (%) | N | (%) | |
| Adults and children >6 | | | | | | | | | |
| CT ≥20 | 33 | (85%) | 6 | (15%) | 171 | (70%) | 75 | (30%) | 0.05 |
| [20-25[ | 20 | (77%) | 6 | (23%) | 95 | (63%) | 58 | (37%) | |
| ≥ 25 | 13 | (100%) | 0 | (0%) | 76 | (81%) | 18 | (19%) | |
| CT <20 | 2 | (7%) | 26 | (93%) | 35 | (15%) | 197 | (85%) | 0.26 |
| Children ≤6 | | | | | | | | | |
| CT ≥20 | 2 | (50%) | 2 | (50%) | 13 | (39) | 20 | (61) | 0.68 |
| [20-25[ | 0 | (0%) | 1 | (100%) | 5 | (29) | 12 | (71) | |
| ≥ 25 | 2 | (66%) | 1 | (34%) | 8 | (50) | 8 | (50) | |
| CT <20 | 1 | (14%) | 6 | (86%) | 6 | (21) | 23 | (79) | 0.70 |

Figure 4

|  | Baseline | Outcome | | | | Highest recorded value, µM (all patients) | | |
|---|---|---|---|---|---|---|---|---|
| Baseline | N (column %)* | Death N (row %) | | Cured N (row %) | | <110 N (OT %) | 110-299 N (OT %) | ≥300 N (OT %) |
| Overall | | | | | | | | |
| <110 µM | 24 (49%) | 6 | (25%) | 18 | (75%) | 20 | 1[1] | 3[1] |
| 110-299 µM | 20 (20%) | 10 | (50%) | 10 | (50%) | - | 17 | 3 |
| ≥300 µM | 16 (8%) | 13 | (81%) | 3 | (19%) | - | - | 16 |
| Missing** | 9 | 4 | | 5 | | 5 | 0 | 2 |
| Overall | 69 | 33 | (48%) | 36 | (52%) | 25 (36%) | 18 (27%) | 24 (36%) |
| Baseline CT ≥20 | | | | | | | | |
| <110 µM | 19 (49%) | 3 | (16%) | 16 | (84%) | 18 | 0 | 1 |
| 110-299 µM | 10 (26%) | 0 | (0%) | 10 | (100%) | - | 10 | 0 |
| ≥300 µM | 4 (10%) | 1 | (25%) | 3 | (75%) | - | - | 4 |
| Missing** | 6 | 2 | | 4 | | 4 | 0 | 2 |
| Overall | 39 (100%) | 6 | (15%) | 33 | (85%) | 22 (33%) | 11 (16%) | 7 (10%) |
| Baseline CT <20 | | | | | | | | |
| <110 µM | 5 (18%) | 3 | (60%) | 2 | (40%) | 2 | 1 | 2 |
| 110-299 µM | 10 (36%) | 10 | (100%) | 0 | (0%) | - | 7 | 3 |
| ≥300 µM | 12 (43%) | 12 | (100%) | 0 | (0%) | - | - | 12 |
| Missing** | 1 | 1 | | 0 | | - | - | - |
| Overall | 28 (100%) | 26 | (93%) | 2 | (7%) | 2 (3%) | 8 (12%) | 17 (25%) |

Figure 5

|  | Overall | Baseline CT ≥20 | Baseline CT <20 | Highest recorded value µM (all patients) † |  |  |  | Death | Last recorded value, µM (patients cured only) † |  |  |  |
|---|---|---|---|---|---|---|---|---|---|---|---|---|
|  |  |  |  | 1 | 2 | 3 | 4 |  | 1 | 2 | 3 | 4 |
| ASAT, baseline |  |  |  |  |  |  |  |  |  |  |  |  |
| Mean (SD) | 838 (738) | 513 (560) | 1438 (657) |  |  |  |  |  |  |  |  |  |
| 1  <50 IU, N (%) | 4 (11%) | 4 (17%) | 0 | 2 | 1 [1] | 1 [2] | 0 | 1 | 3 | 0 | 0 | 0 |
| 2  50-500 IU, N (%) | 14 (38%) | 11 (46%) | 3 (23%) | 0 | 12 | 1 [3] | 1 [4] | 4 | 3 | 7* | 0 | 0 |
| 3  500-1000 IU, N (%) | 5 (13%) | 5 (21%) | 0 | 0 | 5 | 0 | 0 | 0 | 2 | 3* | 0 | 0 |
| 4  ≥1000 IU, N (%) | 14 (38%) | 4 (17%) | 10 (77%) | 3 | 0 | 0 | 11 | 10 | 1 | 3* | 0 | 0 |
| ALAT, baseline |  |  |  |  |  |  |  |  |  |  |  |  |
| Mean (SD) | 304 (354) | 140 (129) | 512 (435) |  |  |  |  |  |  |  |  |  |
| 1  <50 IU, N (%) | 10 (23%) | 9 (38%) | 1 (5%) | 2 | 6 [5] | 0 | 0 | 3 | 6 | 1* | 0 | 0 |
| 2  50-500 IU, N (%) | 26 (60%) | 14 (58%) | 12 (63%) | 2 | 24 | 0 | 0 | 12 | 14 | 0 | 0 | 0 |
| 3  500-1000 IU, N (%) | 4 (9%) | 1 (4%) | 3 (16%) | 0 | 1 | 3 | 0 | 1 | 1 | 0 | 0 | 0 |
| 4  ≥1000 IU, N (%) | 3 (7%) | 0 | 3 (16%) | 0 | 0 | 1 | 2 | 3 | . | . | . | . |
| Ratio ASAT/ALAT | 4 (2) | 4 (4) | 5 (1) |  |  |  |  |  |  |  |  |  |
| Creatine kinase, baseline |  |  |  |  |  |  |  |  |  |  |  |  |
| Mean (SD) | 2042 (1559) | 1621 (1397) | 2547 (1625) |  |  |  |  |  |  |  |  |  |
| 1  <400 IU, N (%) | 5 (11%) | 5 (21%) | 0 | 3 | 1 | 1 | 0 | 2 | 3 | 0 | 0 | 0 |
| 2  400-2000 IU, N (%) | 19 (43%) | 9 (37%) | 10 (50%) | 5 | 12 | 2 | 0 | 10 | 9 | 0 | 0 | 0 |
| 3  2000-4000 IU, N (%) | 12 (27%) | 8 (33%) | 4 (20%) | 5 | 3 | 4 | 0 | 4 | 7 | 1 | 0 | 0 |
| 4  >4000 IU, N (%) | 8 (18%) | 2 (8%) | 6 (30%) | 0 | 1 | 1 | 6 | 6 | 1 | 1 | 0 | 0 |

Figure 6

METHODS AND PHARMACEUTICAL COMPOSITIONS FOR THE TREATMENT OF EBOLA VIRUS DISEASE

FIELD OF THE INVENTION

The invention is in the field of medicine. More particularly, the invention relates to methods and pharmaceutical compositions for the treatment of Ebola Virus Disease.

BACKGROUND OF THE INVENTION

The Ebola virus comes from the Filoviridae family, similar to the Marburg virus. It is named after the Ebola River in Zaire, Africa, near where the first outbreak was noted by Dr. Ngoy Mushola in 1976 after a significant outbreaks in both Yambuku, Zaire (now the Democratic Republic of the Congo), and Nzara, in western Sudan. There are three distinct species of Ebola virus which cause fatal disease in humans: Zaire ebolavirus (ZEBOV) (also known as EBOV), Sudan ebolavirus (SEBOV) and Ivory Coast ebolavirus (ICEBOV).

Among humans, the Ebola virus is transmitted by direct contact with infected body fluids such as blood. The incubation period of Ebola virus infection varies from two days to four weeks. Symptoms are variable too, but the onset is usually sudden and characterised by high fever, prostration, myalgia, arthralgia, abdominal pains and headache. These symptoms progress to vomiting, diarrhea, oropharyngeal lesions, conjunctivitis, organ damage (notably the kidney and liver) by co-localized necrosis, proteinuria, and bleeding both internal and external, commonly through the gastrointestinal tract. Death or recovery to convalescence occurs within six to ten days of onset of symptomology.

Although several antivirals have shown efficacy against Ebola virus infection in vitro or in animal models, none of them have been yet assessed in human beings with Ebola virus disease. Thus, there exists a hurge need in the art for an effective curative treatment against Ebola Virus Disease. Potential drug candidates include Favipiravir a nucleotide analogue approved for novel or re-emerging influenza in Japan (Furuta et al., 2013).

Indeed, results of two independent studies in mice infected with Ebola virus recently showed that the initiation of 150 mg/kg Favipiravir twice a day within 6 days of infection induced rapid virus clearance, reduced biochemical parameters of disease severity, and led to 100% survival (Smither et al., 2014 and Oestereich et al., 2014).

SUMMARY OF THE INVENTION

The invention relates to methods and pharmaceutical compositions for the treatment of Ebola Virus Disease. In particular, the present invention is defined by the claims.

DETAILED DESCRIPTION OF THE INVENTION

The inventors have now demonstrated that Favipiravir (T-705; 6-fluoro-3-hydroxy-2-pyrazinecarboxamide) represents an effective curative strategy in human subjects, especially in Ebola-infected subjects having a weak viral load.

Accordingly a first object of the present invention relates to a method of treating Ebola Virus Disease in a subject in need thereof comprising administering the subject with a therapeutically effective amount of Favipiravir.

As used herein, the term "Ebola virus" refers to a member of the family Filoviridae, are associated with outbreaks of highly lethal hemorrhagic fever in humans and nonhuman primates. Human pathogens include Ebola Zaire, Ebola Sudan, and Ebola Ivory Coast. Ebola Reston is a monkey pathogen and is not considered a significant human pathogen. The natural reservoir of the virus is unknown and there are currently no available vaccines or effective therapeutic treatments for filovirus infections. The genome of Ebola virus consists of a single strand of negative sense RNA that is approximately 19 kb in length. This RNA contains seven sequentially arranged genes that produce 8 mRNAs upon infection. Ebola virions, like virions of other filoviruses, contain seven proteins: a surface glycoprotein (GP), a nucleoprotein (NP), four virion structural proteins (VP40, VP35, VP30, and VP24), and an RNA-dependent RNA polymerase (L) (Feldmann et al. (1992) Virus Res. 24, 1-19; Sanchez et al., (1993) Virus Res. 29, 215-240; reviewed in Peters et al. (1996) In Fields Virology, Third ed. pp. 1161-1176. Fields et al. eds. Lippincott-Raven Publishers). The glycoprotein of Ebola virus is unusual in that it is encoded in two open reading frames. Transcriptional editing is needed to express the transmembrane form that is incorporated into the virion (Sanchez et al. (1996) Proc. Natl. Acad. Sci. USA 93, 3602-3607; Volchkov et al, (1995) Virology 214, 421-430).

In some embodiments of the invention, said Ebola virus is Ivory Coast Ebola virus (ICEBOV), Zaire Ebola virus (ZEBOV or EBOV), Sudan Ebola Virus (SEBOV), or a new strain or species of Ebola virus.

As used herein, the term "Ebola virus disease" (EVD), formerly known as Ebola haemorrhagic fever, is a severe, often fatal illness in humans. The incubation period, that is, the time interval from infection with the virus to onset of symptoms is 2 to 21 days. Humans are not infectious until they develop symptoms. First symptoms are the sudden onset of fever fatigue, muscle pain, headache and sore throat. This is followed by vomiting, diarrhoea, rash, symptoms of impaired kidney and liver function, and in some cases, both internal and external bleeding (e.g. oozing from the gums, blood in the stools). Laboratory findings include low white blood cell and platelet counts and elevated liver enzymes.

As used herein, the term "treatment" or "treat" refer to both prophylactic or preventive treatment as well as curative or disease modifying treatment, including treatment of subjects at risk of contracting the disease or suspected to have contracted the disease as well as subjects who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

In some embodiments, the subject is infected, or is at risk of being infected with Ebola. Diagnosis may be performed by any suitable means. One skilled in the art will understand that a subject to be treated according to the present invention may have been identified using standard tests or may have been identified, without examination, as one at high risk due to the presence of one or more risk factors (e.g., exposure to Ebola virus, etc.). In some embodiments, the subject is infected but is asymptomatic (i.e. the symptoms are not detected). In some embodiments, the diagnosis is performed by detecting Ebola virus nucleic acids in a sample obtained from the subject by any method familiar to one of skill in the art. Such methods typically include the methods based on the detecting the Ebola virus nucleic acids expression. Ebola virus nucleic acids may be detected in a RNA sample, preferably after amplification. For instance, the isolated RNA may be subjected to coupled reverse transcription and amplification, such as reverse transcription and amplification by polymerase chain reaction (RT-PCR), using specific oligonucleotide primers that are specific for a Ebola virus nucleic acid (e.g. those encoding the nucleoprotein (NP) and the four virion structural proteins (VP40, VP35, VP30, and VP24). For instance, a RT-PCR Assay is intended for the in vitro qualitative detection of Ebola virus RNA in clinical specimens, including whole blood, serum, plasma, and urine, from individuals meeting Ebola virus clinical and/or epidemiological criteria (for example, clinical signs and symptoms associated with Ebola, contact with a probable or confirmed Ebola virus case, history of travel to geographic locations where Ebola virus cases were detected, or other epidemiologic links for which Ebola virus testing may be indicated as part of a public health investigation).

In some embodiment, the method of the present invention comprises the step of i) determining the viral load in a sample obtained from the subject ii) comparing the viral load determined at step i) with a predetermined reference value and iii) administering the subject with a therapeutically effective amount of Favipiravir when the viral load determined at step i) is lower than the predetermined reference value.

As used herein, the term "sample" refers to a biological sample obtained for the purpose of in vitro evaluation. In the methods of the invention, the sample may comprise any body fluid obtained from a subject. In some embodiments, the sample is a bodily fluid such as peripheral blood, cord blood, urine, cerebrospinal fluid, saliva, and lymph. Typical biological samples to be used in the method according to the invention are blood samples (e.g. whole blood sample, serum sample, or plasma sample). A biological sample can be optionally pre-treated or processed prior to be used. Examples of pre-treatment steps include the addition of a reagent such as a stabilizer, a preservative, a fixant, a lysing reagent, a diluent, an anti-apoptotic reagent, a buffering reagent, an osmolarity regulating reagent, a pH regulating reagent, and/or a cross-linking reagent. Thus, a sample, can be analyzed under any of the methods and systems herein within 1 week, 6 days, 5 days, 4 days, 3 days, 2 days, 1 day, 12 hrs, 6 hrs, 3 hrs, 2 hrs, or 1 hr from the time the sample is obtained. In some embodiments, RNA are extracted from the sample. Conventional methods and reagents for isolating RNA from a sample comprise Trizol (Invitrogen), Guanidinium thiocyanate-phenol-chloroform extraction, PureLink™ miRNA isolation kit (Invitrogen), PureLink Micro-to-Midi Total RNA Purification System (invitrogen), RNeasy kit (Qiagen), Oligotex kit (Qiagen), phenol extraction, phenol-chloroform extraction, TCA/acetone precipitation, ethanol precipitation, Column purification, Silica gel membrane purification, PureYield™ RNA Midiprep (Promega), PolyATtract System 1000 (Promega), Maxwell® 16 System (Promega), SV Total RNA Isolation (Promega), geneMAG-RNA/DNA kit (Chemicell), TRI Reagent® (Ambion), RNAqueous Kit (Ambion), ToTALLY RNA™ Kit (Ambion), Poly(A)Purist™ Kit (Ambion) and any other methods, commercially available or not, known to the skilled person.

The term "viral load" as used herein refers to the amount of Ebola viral particles present in the sample obtained from the subject. "Viral load" encompasses all Ebola viral particles, infectious, replicative and non-infective, and fragments thereof. Therefore, viral load represents the total number of viral particles thereof circulating in the biological fluid. Viral load can therefore be a measure of any of a variety of indicators of the presence of Ebola virus, such as viral copy number per unit of sample, units of viral proteins or fragments thereof per unit sample, or viral RNA copies per unit of sample. In some embodiments, the Ebola viral load is determined at the protein or nucleic acid level, using, for example, immunochemistry techniques or nucleic acid-based techniques such as in situ hybridization and RT-PCR. In some embodiments, the viral load is determined on a protein level using, for example, antibodies that are directed against viral proteins. These antibodies are used in various methods such as ELISA or multiplexing technologies. In some embodiments, the Ebola viral load is determined at nucleic acid level, in particular RNA level. Methods for determining the quantity of RNA (e.g. mRNA) are well known in the art. For example the nucleic acid contained in the biological samples is first extracted according to standard methods, for example using lytic enzymes or chemical solutions or extracted by nucleic-acid-binding resins following the manufacturer's instructions. The extracted mRNA is then detected by hybridization (e.g., Northern blot analysis) and/or amplification (e.g., RT-PCR). Quantitative or semi-quantitative RT-PCR is preferred. Real-time quantitative or semi-quantitative RT-PCR is particularly advantageous. Nucleic acids having at least 10 nucleotides and exhibiting sequence complementarity or homology to the mRNA of interest herein find utility as hybridization probes. It is understood that such nucleic acids need not be identical, but are typically at least about 80% identical to the homologous region of comparable size, more preferably 85% identical and even more preferably 90-95% identical. Probes typically comprise single-stranded nucleic acids of between 10 to 1000 nucleotides in length, for instance of between 10 and 800, more preferably of between 15 and 700, typically of between 20 and 500. The probes and primers are "specific" to the nucleic acids they hybridize to, i.e. they preferably hybridize under high stringency hybridization conditions (corresponding to the highest melting temperature Tm, e.g., 50% formamide, 5× or 6×SCC. SCC is a 0.15 M NaCl, 0.015 M Na-citrate). In the context of the invention, "hybridization" relates to the fact of obtaining a close interaction of the nucleotide probe and the target region that is expected to be revealed by the detection of the nucleotide probe. Such an interaction can be achieved by the formation of hydrogen bonds between the nucleotide probe and the target sequence, which is typical of the interactions between complementary nucleotide molecules capable of base pairing. Hydrogen bonds can be found, for example, in the annealing of two complementary strands of DNA. It will be advantageous to use nucleic acids in combination with appropriate means, such as a detectable label, for detecting hybridization. A wide variety of appropriate indicators are known in the art including, fluorescent, radioactive, enzymatic or other ligands. In a real time PCR assay a positive reaction is detected by accumulation of a fluorescent signal. The CT (cycle threshold) is defined as the number of cycles required for the fluorescent signal to cross the threshold (ie exceeds background level). CT levels are inversely proportional to the amount of target nucleic acid in the sample (ie the lower the CT level the greater the amount of target nucleic acid in the sample). Accordingly, in some embodiments of the invention, the viral load in a sample obtained from the subject is determined by virtue of the CT (cycle threshold).

In some embodiments, the RT-PCR is performed with the RealStar® Ebolavirus RT-PCR Kit 1.01 kit commercially available from Altona Diagnostics GmbH (Morkenstr. 12, 22767 Hamburg, Germany) which is suitable for the presumptive detection of RNA from Ebolavirus (including Zaire ebolavirus detected in the West Africa outbreak in 2014) on specified instruments in EDTA plasma specimens from individuals with signs and symptoms of Ebolavirus infection in conjunction with epidemiological risk factors. The test is based on real-time RT-PCR technology, utilizing reverse transcriptase (RT) reaction to convert RNA into complementary DNA (cDNA), polymerase chain reaction (PCR) for the amplification of specific target sequences and target specific probes for the detection of the amplified DNA. The probes are labelled with fluorescent reporter and quencher dyes. Probes specific for Ebolavirus RNA are labeled with the fluorophore FAM. The probe specific for the target of the Internal Control (IC) is labeled with the fluorophore JOE. Using probes linked to distinguishable dyes enables the parallel detection of Ebolavirus specific RNA and the Internal Control in the corresponding detector channels of the real-time PCR instrument. The RealStar® Ebolavirus RT-PCR Kit 1.0 consists of Two Master reagents (Master A and Master B); Template Internal Control (IC) Positive Control Target EBOLA; •PCR grade water. Master A and Master B reagents contain all components (buffer, enzymes, primers, and probes) to allow reverse transcription, PCR mediated amplification and target detection (Ebolavirus specific RNA and Internal Control) in one reaction setup. The Internal Control contains a defined copy number of an "artificial" RNA molecule with no homologies to any other known sequences. It has to be added to the nucleic acid extraction procedure and is reverse transcribed, amplified and detected in parallel to the Ebolavirus specific RNA. The function of the Internal Control is to ensure the integrity of Ebolavirus specific real-time RTPCR results by indicating potential RT-PCR inhibition. The PCR grade water is to be used as negative control for the RT-PCR-reaction. Its function is to indicate contamination of RT-PCR reagents. The "Positive Control Target EBOLA" consists of an in vitro transcript which contains the target sequence used by the RealStar® Ebolavirus RT-PCR Kit 1.0 for the detection of Ebolavirus specific RNA. The "Positive Control Target EBOLA" is used as positive control for the RT-PCR and verifies the functionality of the Ebolavirus RNA specific RT-PCR detection system, which is included in the RealStar® Ebolavirus RT-PCR Kit 1.0. Typically, the workflow starts with taking EDTA whole blood from the subject. Separation of cellular. Material and devices required for performing the test typically required appropriate real-time PCR instrument such as ABI Prism® 7500 SDS (Applied Biosystems, Cat No. 4351104), ABI Prism® 7500 Fast SDS (Applied Biosystems, Cat No. 4351106, LightCycler® 480 Instrument II (Roche, Cat No. 05015278001), CFX96™ system/Dx real-time system (BIO-RAD, Cat. No. 185-5195); Appropriate nucleic acid extraction system or kit such as QIAamp® Viral RNA Mini Kit (QIAGEN, Cat. No. 52906 or 52904), Desktop centrifuge with a rotor for 2 ml reaction tubes (Eppendorf 5415C orequivalent); Centrifuge with a rotor for microtiter plates, if using 96 well reaction plates; Vortex mixer (VWR 58810-163 or equivalent); Appropriate 96 well reaction plates or reaction tubes with corresponding (optical) closing material; Nuclease-Free Water (not DEPC-Treated), Life Technologies (Cat. No 4387936) or equivalent.

As used herein, the term "predetermined reference value" refers to the viral load in samples obtained from the general population or from a selected population of subjects. Typically, the predetermined reference value is a threshold value or a cut-off value. A "threshold value" or "cut-off value" can be determined experimentally, empirically, or theoretically. A threshold value can also be arbitrarily selected based upon the existing experimental and/or clinical conditions, as would be recognized by a person of ordinary skilled in the art. In some embodiments, the threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. For example, after determining the viral load in a group of reference, one can use algorithmic analysis for the statistic treatment of the expression levels determined in samples to be tested, and thus obtain a classification standard having significance for sample classification. The full name of ROC curve is receiver operator characteristic curve, which is also known as receiver operation characteristic curve. It is mainly used for clinical biochemical diagnostic tests. ROC curve is a comprehensive indicator the reflects the continuous variables of true positive rate (sensitivity) and false positive rate (1-specificity). It reveals the relationship between sensitivity and specificity with the image composition method. A series of different cut-off values (thresholds or critical values, boundary values between normal and abnormal results of diagnostic test) are set as continuous variables to calculate a series of sensitivity and specificity values. Then sensitivity is used as the vertical coordinate and specificity is used as the horizontal coordinate to draw a curve. The higher the area under the curve (AUC), the higher the accuracy of diagnosis. On the ROC curve, the point closest to the far upper left of the coordinate diagram is a critical point having both high sensitivity and high specificity values. The AUC value of the ROC curve is between 1.0 and 0.5. When AUC>0.5, the diagnostic result gets better and better as AUC approaches 1. When AUC is between 0.5 and 0.7, the accuracy is low. When AUC is between 0.7 and 0.9, the accuracy is moderate. When AUC is higher than 0.9, the accuracy is quite high. This algorithmic method is preferably done with a computer. Existing software or systems in the art may be used for the drawing of the ROC curve, such as: MedCalc 9.2.0.1 medical statistical software, SPSS 9.0, ROCPOWER.SAS, DESIGN-ROC.FOR, MULTIREADER POWER.SAS, CREATE-ROC.SAS, GB STAT VI0.0 (Dynamic Microsystems, Inc. Silver Spring, Md., USA), etc. In some embodiments, the predetermined reference value correlates with the viral load for which the subject would achieve a response with the treatment (i.e. Favipiravir). In particular it is considered that the subject achieves a response with the treatment when he survives (e.g. the subject is cured) and it is considered that the subject does not achieve a response when he does not survive (i.e dead). In some embodiments, the predetermined reference value is typically determined by carrying out a method comprising the steps of:

a) providing a collection of blood samples from subject suffering from Ebola virus disease and administered with Favipiravir;

b) providing, for each blood sample provided at step a), information relating to the actual clinical outcome for the corresponding subject (i.e. the duration of the disease-free survival (DFS) and/or the overall survival (OS));

c) providing a serial of arbitrary quantification values;

d) determining the viral load for each blood sample contained in the collection provided at step a);

e) classifying said blood samples in two groups for one specific arbitrary quantification value provided at step c), respectively: (i) a first group comprising blood samples that exhibit a quantification value for level that is lower than the said arbitrary quantification value contained in the said serial of quantification values; (ii) a second group comprising blood samples that exhibit a quantification value for said level that is higher than the said arbitrary quantification value contained in the said serial of quantification values; whereby two groups of blood samples are obtained for the said specific quantification value, wherein the blood samples of each group are separately enumerated;

f) calculating the statistical significance between (i) the quantification value obtained at step e) and (ii) the actual clinical outcome of the subjects from which blood samples contained in the first and second groups defined at step f) derive;

g) reiterating steps f) and g) until every arbitrary quantification value provided at step d) is tested;

h) setting the said predetermined reference value as consisting of the arbitrary quantification value for which the highest statistical significance (most significant) has been calculated at step g).

For example the viral load has been assessed for 100 blood samples of 100 subjects. The 100 samples are ranked according to the determined viral load. Sample 1 has the highest level and sample 100 has the lowest level. A first grouping provides two subsets: on one side sample Nr 1 and on the other side the 99 other samples. The next grouping provides on one side samples 1 and 2 and on the other side the 98 remaining samples etc., until the last grouping: on one side samples 1 to 99 and on the other side sample Nr 100. According to the information relating to the actual clinical outcome for the corresponding subject, Kaplan Meier curves are prepared for each of the 99 groups of two subsets. Also for each of the 99 groups, the p value between both subsets was calculated. The predetermined reference value is then selected such as the discrimination based on the criterion of the minimum p value is the strongest. In other terms, the viral load corresponding to the boundary between both subsets for which the p value is minimum is considered as the predetermined reference value. It should be noted that the predetermined reference value is not necessarily the median value of levels of viral RNA. Thus in some embodiments, the predetermined reference value thus allows discrimination between a poor and a good prognosis with respect to DFS and OS for a subject. Practically, high statistical significance values (e.g. low P values) are generally obtained for a range of successive arbitrary quantification values, and not only for a single arbitrary quantification value. Thus, in one alternative embodiment of the invention, instead of using a definite predetermined reference value, a range of values is provided. Therefore, a minimal statistical significance value (minimal threshold of significance, e.g. maximal threshold P value) is arbitrarily set and a range of a plurality of arbitrary quantification values for which the statistical significance value calculated at step g) is higher (more significant, e.g. lower P value) are retained, so that a range of quantification values is provided. This range of quantification values includes a “cut-off” value as described above. For example, according to this specific embodiment of a “cut-off” value, the outcome can be determined by comparing the viral load with the range of values which are identified. In some embodiments, a cut-off value thus consists of a range of quantification values, e.g. centered on the quantification value for which the highest statistical significance value is found (e.g. generally the minimum p value which is found). For example, on a hypothetical scale of 1 to 10, if the ideal cut-off value (the value with the highest statistical significance) is 5, a suitable (exemplary) range may be from 4-6. Therefore, a subject may be assessed by comparing values obtained by measuring the viral load, where values lower than 5 reveal that the subject can be administered with the drug (i.e. the subject will achieve a response with Favipiravir) and values higher than 5 reveal the subject cannot be administered whit the drug (i.e. the subject will not achieve a response with Favipiravir). In some embodiments, a subject may be assessed by comparing values obtained by measuring the viral load and comparing the values on a scale, where values below the range of 4-6 indicate the subject can be administered with the drug (i.e. the subject will achieve a response with Favipiravir) and values above the range of 4-6 indicate that the subject cannot be administered whit the drug (i.e. the subject will not achieve a response with Favipiravir).

In some embodiments, when the viral load is determined by RT-PCT and in particular with the RealStar® Ebolavirus RT-PCR Kit 1.01 kit, the predetermined value is the level of viral RNA for which the CT (cycle threshold) is 20. Accordingly when the level of viral RNA is lower than this predetermined value (i.e. the CT value is higher than 20), the subject is administered with the therapeutically effective amount of Favipiravir and when the level of viral RNA is higher than this predetermined value (i.e. the CT value is lower than 20), the subject is not administered with the therapeutically effective amount of Favipiravir.

When the subject is not treated with Favipiravir, he can follow basic interventions, that when used early, can significantly improve the chances of survival. Such basic interventions include, providing intravenous fluids (IV) and balancing electrolytes (body salts), maintaining oxygen status and blood pressure and treating other infections if they occur.

As used herein, the term “Favipiravir” refers to 6-fluoro-3-hydroxy-2-pyrazinecarboxamide (also known as T-705) which is a compound useful for the prevention and treatment of viral infectious diseases, particularly influenza viral infectious diseases. Favipiravir is a nucleotide analogue approved for novel or re-emerging influenza in Japan (Furuta et al., 2013). Said compound is extensively described in the European Patent no EP1112743B1 as well as methods for obtaining said compound. European Patent no EP2407166B1 describes tablet which contains a high quantity of 6-fluoro-3-hydroxy-2-pyrazinecarboxamide or a salt thereof and has superior release characteristics.

In some embodiments, a salt of Favipiravir is administered, preferably an organic amine salt. The term "organic amines" refers to tertiary amines such as trimethylamine, triethylamine, tripropylamine, tributylamine, tribenzylamine and N,N-dimethylcyclohexylamine; secondary amines such as dimethylamine, diethylamine, dipropylamine, dibutylamine, dibenzylamine, N-benzylmethylamine and dicyclohexylamine; primary amines such as methylamine, ethylamine, propylamine, butylamine, benzylamine and aniline; and pyridine and the like.

By a "therapeutically effective amount" of Favipiravir is meant a sufficient amount of Favipiravir to treat Ebola Virus Disease, at a reasonable benefit/risk ratio applicable to any medical treatment. It will be understood, however, that the total daily usage of Favipiravir of will be decided by the attending physician within the scope of sound medical judgment. The specific therapeutically effective dose level for any particular subject will depend upon a variety of factors including the disorder being treated and the severity of the disorder; activity of the specific antibody employed; the specific composition employed, the age, body weight, general health, sex and diet of the subject; the time of administration, route of administration, and rate of excretion of the specific antibody employed; the duration of the treatment; drugs used in combination or coincidental with Favipiravir; and like factors well known in the medical arts. For example, it is well known within the skill of the art to start doses of the compound at levels lower than those required to achieve the desired therapeutic effect and to gradually increase the dosage until the desired effect is achieved. Usually, 10 to 5,000 mg or, preferably 200 to 2,400 mg of Favipiravir may be administered per day to an adult once or several times in installments. Favipiravir may be administered in several dosages or as a single dose until a desired response has been achieved. The treatment is typically monitored and repeated dosages can be administered as necessary. Favipiravir may be administered according to dosage regimens established. In some embodiments, 6,000 mg of Favipiravir are administered the first day (in three times as described in the Example) and 1,200 mg of Favipiravir is administered in the nine consecutive followings days.

Typically, Favipiravir is administered in the form of a pharmaceutical composition. Pharmaceutical compositions comprising Favipiravir for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. In some embodiments, Favipiravir is administered orally. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. In some embodiments, Favipiravir is administered in the form of tablets.

The invention will be further illustrated by the following figures and examples. However, these examples and figures should not be interpreted in any way as limiting the scope of the present invention.

EXAMPLE: JIKI TRIAL—EFFICACY OF FAVIPIRAVIR IN REDUCING MORTALITY IN INDIVIDUALS WITH EBOLA VIRUS DISEASE IN GUINEA

Material & Methods
Detailed Description:

The investigators performed a non-comparative, proof-of-concept, phase II trial in subjects with Ebola Virus Disease (EVD) for which the objectives were to assess the efficacy of high-dosed favipiravir in reducing mortality in humans with EVD. Secondary objectives were to assess the evolution of EBOV plasma RNA and infectious loads under treatment; the tolerance of favipiravir; the viral microdiversity of EBOV, the trough concentrations of favipiravir and factors associated with mortality and toxicity. The trial sponsor was the INSERM. The international coordinating, monitoring and data management centre was the "Mereva" clinical trial unit (CTU), an international team with members affiliated to the Inserm 897 Unit, University of Bordeaux and to the "Pacci/ANRS" research site in Abidjan. Trial coordinating, monitoring and data management activities was coordinated by an International Clinical Project Manager (CPM). In Guinea, where the trial was conducted, a trial country coordination center (CCC) was put in place, lead by a country CPM who worked in close collaboration with the international CPM and with the participating clinical centres. The trial will be conducted and monitored according to a Standard Operating Procedures (SOPs) manual.

The investigators designed the following groups according to age and duration of symptoms*: Group A1: adults with time between first symptoms and first dose of favipiravir≤72 h; Group A2: adults with time between first symptoms and first dose of favipiravir>72 h and Group C: all children>1 year and weighting≥10 kg. Time of first symptom refers to the time of the beginning of any symptom considered to be related to EVD. Symptoms to be considered were: acute onset of fever, severe headache, myalgia, extreme fatigue, vomiting, diarrhoea, abdominal pain, or unexplained hemorrhage. The recruitment in the trial was kept opened in all groups until group A1 reaches 60 participants, unless early termination is recommended by the DSMB. The observed pre-trial mortality was estimated using the three months data (from Aug. 15, 2014 to Nov. 15, 2014) of the MSF database in the Gueckedou EVD centre. Given those estimations, and to remain pragmatic and conservative, we set the pre-trial mortality to 55% for groups A1, A2, C. With 60 participants in group A1, the power to conclude that mortality in the trial was −20% inferior to pre-trial mortality was equal to 89%. Statistical analysis for primary outcome: mortality by Day-14 with 95% CI was reported overall and in each group separately. Day-0 is the day of the first dose of favipiravir. In group A1, if the number of deaths is <24 (40%) out of 60 participants, the upper bound of the 95% CI was <55%. In group A2, if the number of deaths is <54 (45%) out of 120 participants, the upper bound of the 95% CI was <55%. In group C, if the number of deaths was <17 (38%) out of 45 participants, the upper bound of the 95% CI would be <55% In each group, the investigator would conclude that favipiravir decreases mortality if the upper bound of the 95% CI does not include the observed pre-trial mortality in untreated subjects with same duration of symptoms prior to trial initiation.

The evolution of EBOV plasma RNA and infectious loads between Day-0 and the end of follow up was described in each subject. The numbers, proportions and exact 95% CI was described for grade 3-4 adverse events; resistance mutations; and subjects reaching criteria for cure at Day-30. The distribution (median, IQR, min-max) of initial and maximal viral load, time to maximal viral load and to undetectability, and rate of increase/decrease was reported. The distribution of trough concentrations of favipiravir at each point and the inter- and intra-subject variability of concentrations was described. Factors associated with mortality by Day-14, cure at Day-30 and grade 3-4 clinical or biological adverse events (including time between first symptoms and treatment initiation, evolution of EBOV viral load, trough concentrations of favipiravir) were studied.

Favipiravir was administered orally:oral administration, 200 mg light yellow, round-shaped, coated divisible tablets that can be crushed and mixed with liquid.

Assigned Interventions:
 Drug: Favipiravir
  Group A1: Day-0 (inclusion), h0: 2400 mg; h8: 2400 mg; h16: 1200 mg. Day-1 to Day-9: 1200 mg bid.
  Group A2: Day-0 (inclusion), h0: 2400 mg; h8: 2400 mg; h16: 1200 mg. Day-1 to Day-9: 1200 mg bid.
  Group C: daily dosages were adapted to their body weight.
 Other Name: AVIGAN Eligibility:
 Inclusion Criteria:
age>1 year and weighting≥10 kg,
EVD confirmed by a positive qualitative PCR test,
signed informed consent (signed by the parents/adults guardians in case of minor subject).
 Non Inclusion-Criteria:
pregnancy*,
inability to take the drug (encephalopathy, severe vomiting).
  * Emergency use of favipiravir in pregnant women outside of the trial is envisaged and under evaluation.
In this protocol, the investigators will refer to the following groups according to age and duration of symptoms**:
Group A1: adults with time between first symptoms and first dose of favipiravir≤72 h;
Group A2: adults with time between first symptoms and first dose of favipiravir>72 h;
Group C: all children>1 year and weighting≥10 kg. Time of first symptom refers to the time of the beginning of any symptom considered to be related to EVD.

Symptoms to be considered were: acute onset of fever, severe headache, myalgia, extreme fatigue, vomiting, diarrhoea, abdominal pain, or unexplained hemorrhage.

The division in groups is a matter of analysis, and will not be perceptible by the subjects during the trial process. Subjects in the three groups received the same treatment and were followed under the same procedures, with only two exceptions: the number of additional blood sample collections were lower in group A2 and C (n=2) than in group A1 (n=3) and daily dosages were adapted to the body weight in group C.

Results

The results are depicted in FIGS. 1-6 and clearly show that the response to the treatment depends on the initial viral load.

Favipiravir in Patients with Ebola Virus Disease: Early Results of the JIKI Trial in Guinea Background:

The JIKI trial (Inserm C1463) assesses the benefits of high-dose favipiravir in reducing mortality and decreasing Ebola virus (EBOV) viral load in patients with Ebola virus disease (EVD).

Methods:

JIKI is a phase II trial conducted in 2 Ebola treatment units run by MSF and ALIMA in Guinea. Inclusion criteria are: positive EBOV RT-PCR (Altona, crossing cycle threshold [CT] for positivity≤40), age≥1 year, ability to take oral drugs, and informed consent. Participants are prescribed oral favipiravir (adults: 6000 mg Day [D]0 [H0 2400 mg, H8 2400 mg, H16 1200 mg], and then 1200 mg bid from D1 to 9). The primary endpoint is mortality. Mortality among participants is compared to mortality during the 3 month period preceding trial initiation in the same centers, as recorded in the MSF/EMLab database. On January 22, the DSMB recommended that the investigators present data on the first 69 adults and adolescents.

Figure 1:
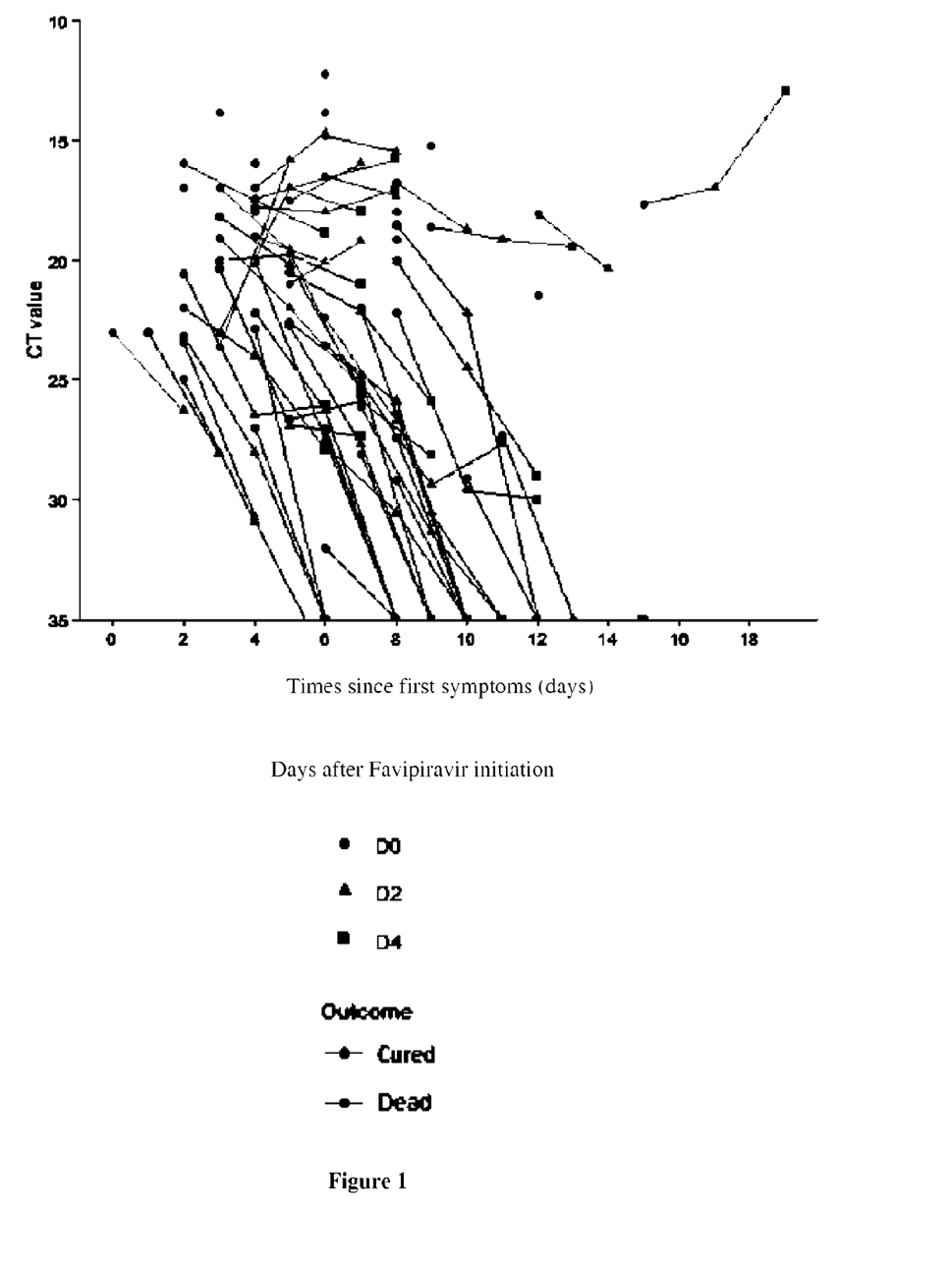
FIG. 1: Evolution of RT-PCR CT values during the first 4 days of treatment with Favipiravir in subjects and children>6 years, JIKI trial (N=69).
Figure 2:
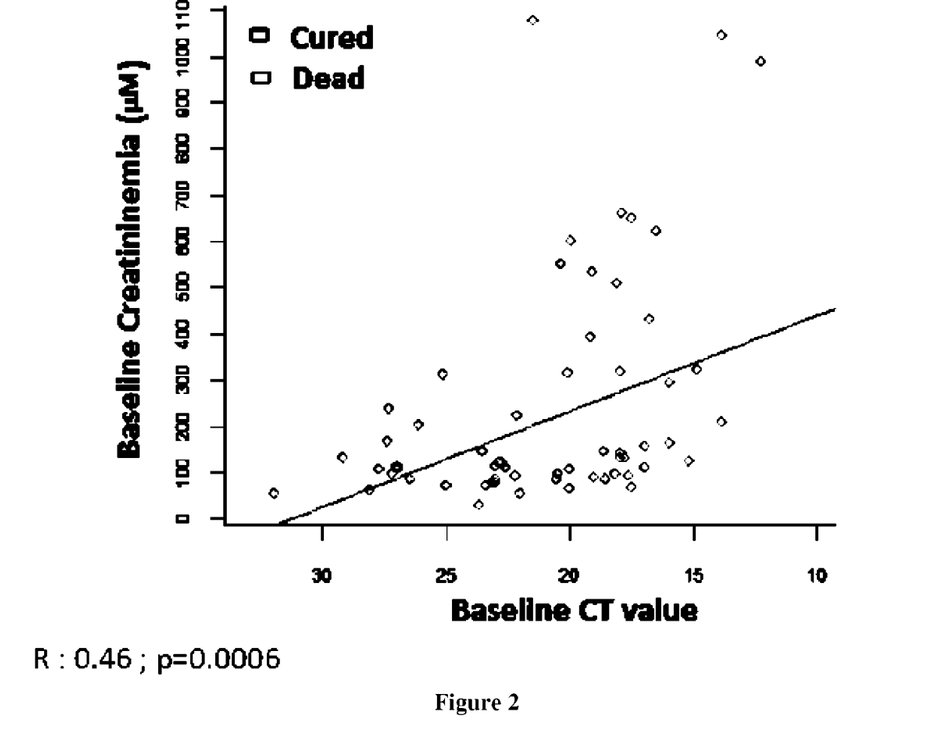
FIG. 2: Correlation between baseline creatinine values and RT-PCR CT values; adults and children>6 years of age, JIKI trial (N=60).
Figure 3:
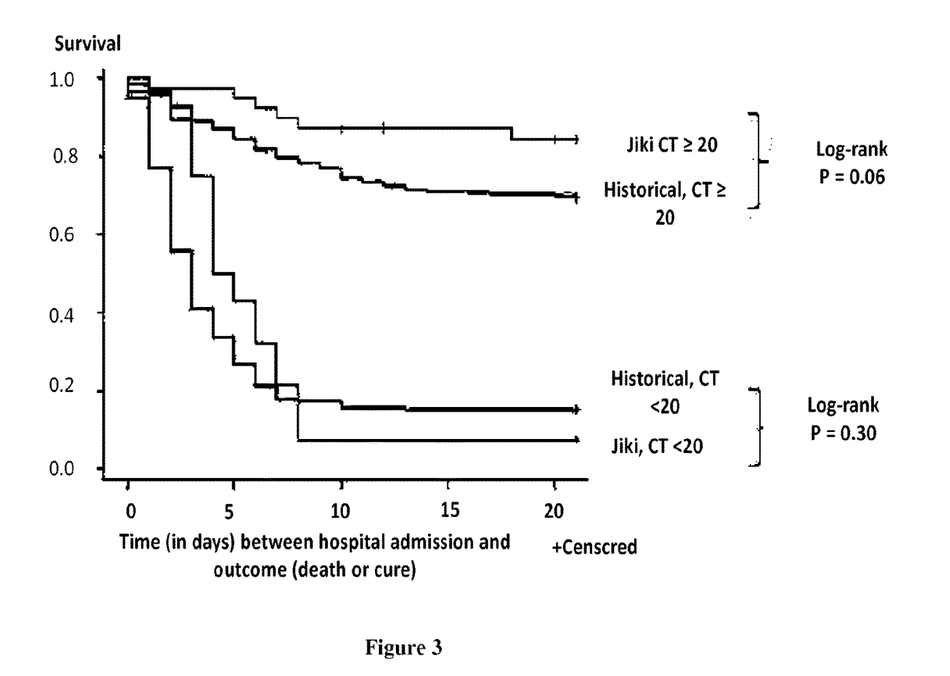
FIG. 3: Value of CT criteria in predicting survival.
Figure 4:
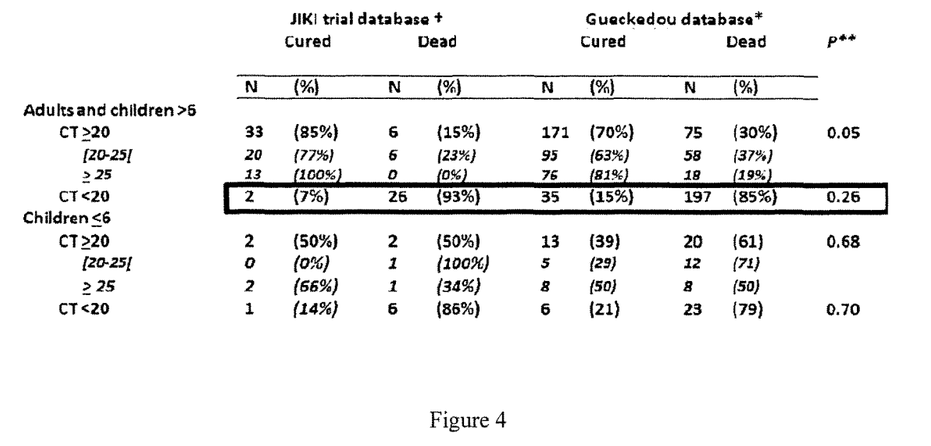
FIG. 4: Mortality by baseline RT-PCR CT value, JIKI trial and Gueckedou databases.
Figure 5:
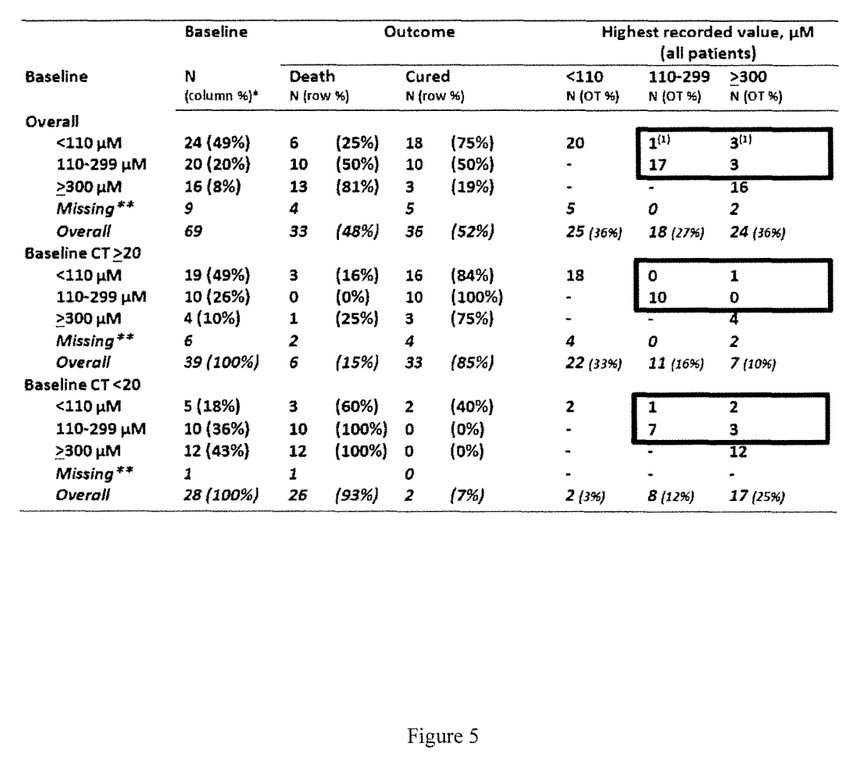
FIG. 5: Creatininemia at baseline and during follow-up, JIKI trial, adults and children>6 years (N=69).
Figure 6:
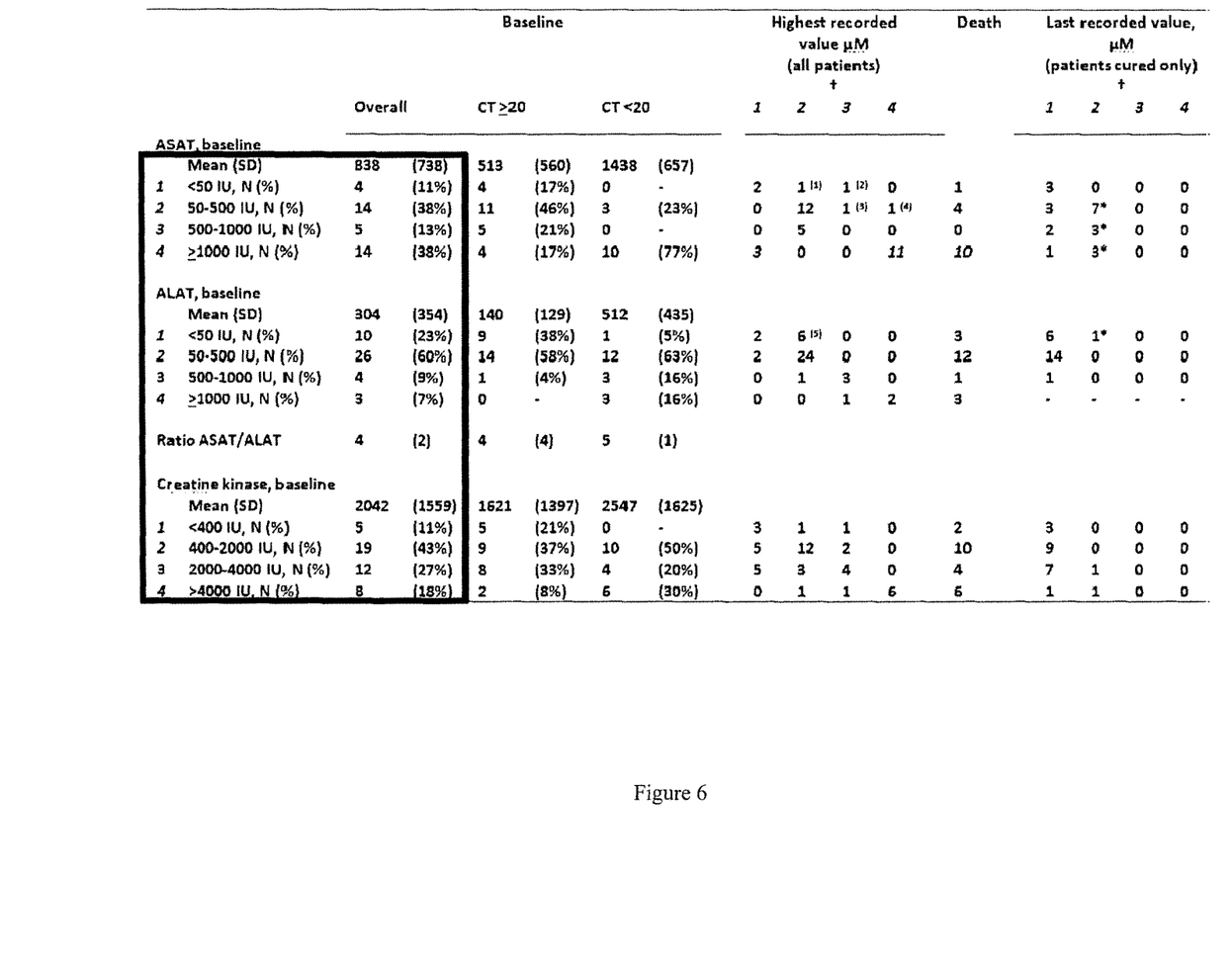
FIG. 6. Transaminases and Creatine Kinase at baseline and during follow-up, JIKI trial, adults and children>6 years (N=69).

Results:

from Dec. 17, 2014 through Jan. 20, 2015, 80 patients received favipiravir, including 69 adults and adolescents≥14 years (women 64%, mean age 38 years, median duration of illness 5 days). The baseline CT (BCT) was <20 in 42% and ≥20 in 58%; the baseline creatinine was ≥110 µM/L in 60% (BCT<20: 79%; BCT≥20: 36%), including ≥300/µM in 27% (BCT<20: 43%; BCT≥20: 10%); baseline ASAT level was ≥1000 IU in 38% (BCT<20: 77%; BCT≥20: 17%); and baseline Creatine Kinase level≥4000 IU in 18% (BCT<20: 24%; BCT≥20: 8%). FIG. 1 shows the PCR CT values at baseline (D0) and at D2 and D4 following treatment initiation. Overall, 48% of participants died (BCT<20: 85%; BCT≥20: 15%). The pre-trial mortality was 58% overall (p=0.15), 85% in patients with BCT<20 (p=0.26) and 30% in patients with BCT≥20 (p=0.05). Mortality was 100% and 7% in patients with abnormal baseline creatinine values and BCT<20 or ≥20, respectively. The drug was well tolerated. Results of quantitative virology and PK tests will be available later.

Conclusions:

In this non comparative proof of concept trial, most patients with CT<20 had severe kidney failure and died, with no indication that favipiravir monotherapy improved survival. Patients with CT≥20 had a lower mortality rate compared to pre-trial figures in the same settings. These preliminary data encourage continued testing of favipiravir with particular attention to identifying patients earlier in disease course, and to explore other therapeutic options, including combinations, in patients who present at advanced stages.

REFERENCES

Throughout this application, various references describe the state of the art to which this invention pertains. The disclosures of these references are hereby incorporated by reference into the present disclosure.

Furuta Y, Gowen B B, Takahashi K, Shiraki K, Smee D F, Barnard D L. Favipiravir (T-705), a novel viral RNA polymerase inhibitor. Antiviral Res 2013; 100: 446-54.

Smither S J, Eastaugh L S, Steward J A, Nelson M, Lenk R P, Lever M S. Post-exposure efficacy of oral T-705 (favipiravir) against inhalational Ebola virus infection in a mouse model. Antiviral Res 2014; 104: 153-55.

Oestereich L, Lüdtke A, Wurr S, Rieger T, Muñoz-Fontela C, Günther S. Successful treatment of advanced Ebola virus infection with T-705 (favipiravir) in a small animal model. Antiviral Res 2014; 105: 17-21.

The invention claimed is:

1. A method of treating Ebola Virus Disease in a subject in need thereof comprising:
   i) determining a viral load in a sample obtained from the subject by RT-PCR;
   ii) comparing the viral load determined at step i) with a predetermined reference value, wherein said predetermined reference value is a level of viral RNA for which the cycle threshold is 20; and
   iii) administering to the subject a therapeutically effective amount of Favipiravir when the viral load determined at step i) is lower than the predetermined reference value.

2. The method of claim 1 wherein Ebola virus is Ivory Coast Ebola virus (ICEBOV), Zaire Ebola virus (ZEBOV or EBOV), Sudan Ebola Virus (SEBOV), or a new strain or species of Ebola virus.

3. The method of claim 1 wherein the sample is a blood sample.

* * * * *